United States Patent [19]

Saeva

[11] Patent Number: 5,302,757
[45] Date of Patent: Apr. 12, 1994

[54] ULTRAVIOLET LIGHT SENSITIVE ONIUM SALTS

[75] Inventor: Franklin D. Saeva, Webster, N.Y.

[73] Assignee: Eastman Kodak Company, Rochester, N.Y.

[21] Appl. No.: 944,640

[22] Filed: Sep. 14, 1992

[51] Int. Cl.$^5$ ............................................. C07C 321/28
[52] U.S. Cl. ..................................... 568/58; 556/427; 560/10; 562/30; 562/45; 562/113; 562/602; 562/607; 564/154; 564/340; 568/13; 568/29; 568/42; 568/49; 568/56; 568/57
[58] Field of Search ................. 568/58, 29, 13, 42, 568/49, 56, 57; 556/427; 560/10; 564/154, 340; 562/30, 45, 113, 602, 607

[56] References Cited

U.S. PATENT DOCUMENTS

| | | | |
|---|---|---|---|
| 4,291,114 | 9/1982 | Berggren et al. | 430/253 |
| 4,380,769 | 4/1983 | Thomas et al. | 346/135.1 |
| 4,485,161 | 11/1984 | Scozzafava et al. | 430/64 |
| 4,547,431 | 10/1985 | Eckberg | 428/413 |
| 4,650,734 | 3/1987 | Molaire et al. | 430/7 |
| 4,661,429 | 4/1987 | Molaire et al. | 430/70 |
| 4,933,377 | 6/1990 | Saeva et al. | 522/31 |
| 5,055,376 | 10/1991 | Saeva | 430/270 |
| 5,089,374 | 2/1992 | Saeva | 430/271 |
| 5,141,969 | 8/1992 | Saeva et al. | 522/31 |

OTHER PUBLICATIONS

*UV Curing: Science and Technology*, S. Peter Pappas, Technology Marketing Corporation, Stamford, Connecticut, 1978.
*Research Disclosure*, vol. 289, May 1988, p. 298, Kenneth Mason Publications Ltd., London, England.
"Synthesis of Sulfonium Salts", *The Chemistry of the Sulfonium Group (Part 1)*, Lowe, P. A., ed. C. J. M. Sterling, John Wiley & Sons, Ltd. (1981), p. 267 et seq.
*Cationic Polymerization of Olefins: A Critical Inventory*, J. P. Kennedy, Wiley Interscience Pub., 1975.

*Primary Examiner*—Richard L. Raymond
*Attorney, Agent, or Firm*—Robert Luke Walker

[57] ABSTRACT

A composition of matter including an onium salt and a method of forming images. The onium salt has a chromophore which absorbs ultraviolet radiation, an S, Se, As, N or P atom which is free of substituents exhibiting a higher energy occupied molecular orbital than the chromophore; an insulating group which links the chromophore to the S, Se, As, N or P atom of the salt and substantially prevents $\pi$ resonance from the chromophore through the S, Se, As, N or P atom; and an anion. The onium salt is capable of forming a Bronsted acid upon exposure to ultraviolet radiation in the presence of a proton source. In the method of forming images, the onium salt is exposed to ultraviolet radiation in the presence of a proton source, to convert said onium salt to a Bronsted acid.

18 Claims, 1 Drawing Sheet

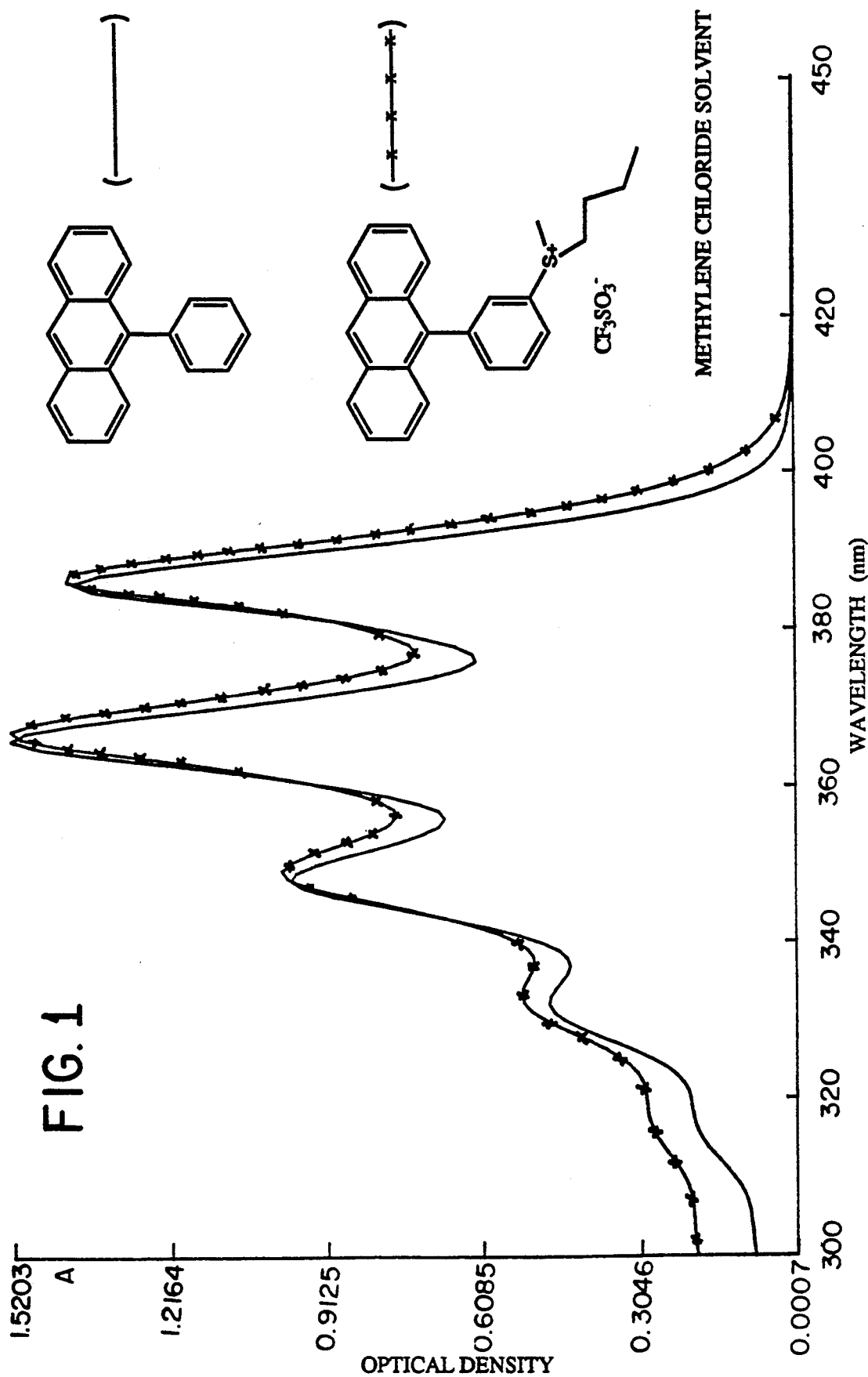

ULTRAVIOLET LIGHT SENSITIVE ONIUM SALTS

FIELD OF THE INVENTION

This invention relates to certain novel onium salts and, more particularly, to ultraviolet light sensitive onium salts. It also relates to the use of such salts as photoinitiators.

BACKGROUND OF THE INVENTION

It is well known that various onium salts, upon exposure to radiation, are capable of forming a Bronsted acid, and that the Bronsted acid thus formed can cure a wide variety of materials. See, for example, *UV Curing: Science and Technology*, edited by S. Peter Pappas and published (1978) by Technology Marketing Corporation, 64 Westover Road, Stamford, Conn. 06902. The problem with such salts is that they do not absorb out to 400 nm, and commonly must be used in combination with a light-absorbing photosensitizer in order to carry out photoinitiation at longer wavelengths than 300 nm.

*Research Disclosure* Vol. 289, May 1988, page 298, published by Kenneth Mason Publications Ltd., London, England, describes sulfonium salts and oxysulfonium salts which, upon exposure to visible radiation, undergo irreversible intramolecular rearrangement to form a Bronsted acid. The light-absorbing capability of these sulfonium and oxysulfonium salts depends upon overlap of molecular orbitals, that is, $\pi$ resonance throughout the molecule. The photo products of these salts absorb at shorter wavelengths than the starting sulfonium and oxysulfonium salts.

European Patent Application 0 447 544, published Sep. 25, 1991, discloses onium salts which form Bronsted acids upon absorption of visible radiation by means of a chromophore joined to the remainder of the molecule by a linkage which interrupts $\pi$ resonance. The chromophore can be selected to match the wavelength of the visible light. The onium salts have; as a substituent on a S, Se, As, N, or P atom in addition to the linked chromophore; at least one electron withdrawing group which exhibits a lower unoccupied molecular orbital than the chromophore.

There is a need in the art for onium salts which absorb ultraviolet radiation, are highly efficient and are thermally stable to the release of acid. It is desirable that such salts be capable of forming a Bronsted acid upon exposure to ultraviolet light of a chromophore joined to the remainder of the molecule through an insulating linkage, since the chromophore could be selected to match the desired exposing radiation.

SUMMARY OF THE INVENTION

In the broader aspects of the invention, there is provided a composition of matter including an onium salt and a method of forming images. The onium salt has a chromophore which absorbs ultraviolet radiation, an S, Se, As, N or P atom which is free of substituents exhibiting a higher energy occupied molecular orbital than the chromophore; an insulating group which links the chromophore to the S, Se, As, N or P atom of the salt and substantially prevents $\pi$ resonance from the chromophore through the S, Se, As, N or P atom; and an anion. The onium salt is capable of forming a Bronsted acid upon exposure to ultraviolet radiation. In the method of forming images, the onium salt is exposed to ultraviolet radiation to convert the onium salt to a Bronsted acid.

It is an advantageous effect of some of the embodiments of the invention that onium salts are provided which are capable of forming a Bronsted acid upon exposure to ultraviolet light of a chromophore joined to the remainder of the molecule through an insulating linkage, are highly efficient, and are thermally stable to the release of acid.

BRIEF DESCRIPTION OF THE DRAWING

The above-mentioned and other features and objects of this invention and the manner of attaining them will become more apparent and the invention itself will be better understood by reference to the following description of an embodiment of the invention taken in conjunction with the accompanying drawing wherein the Figure is an electronic absorption spectra for the onium salt of Example 1 (indicated by an x'ed line) and the free chromophore of Comparative Experiment 1 (indicated by a solid line).

DESCRIPTION OF A SPECIFIC EMBODIMENT

The onium salts of this invention include a S, Se, As, N or P atom, and an ultraviolet sensitive chromophore, that is, a covalently unsaturated group responsible for electronic absorption, which absorbs ultraviolet light. The chromophore is chemically linked to the remainder of the salt by an insulating group which substantially prevents $\pi$ resonance between the chromophore and the rest of the salt. The presence of $\pi$ resonance between the chromophore and the rest of the salt is exhibited by a shift in the electronic absorption peak of a material incorporating a chromophore in comparison to the free chromophore. The onium salts of the embodiment disclosed herein exhibit a shift in absorbance of no more than about 30 nanometers, and in preferred examples, less than 15 nanometers from the electronic absorption of the free chromophore. For example, the Figure shows the electronic absorption spectra for the onium salt of the invention produced in Example 1: 3-(9-anthryl)phenylmethyl-n-butyl sulfonium trifluoromethane sulfonate, which has the structural formula:

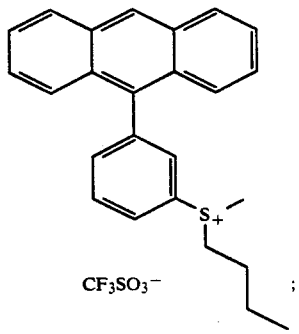

and for the free chromophore: 9-phenylanthracene, which has the structural formula,

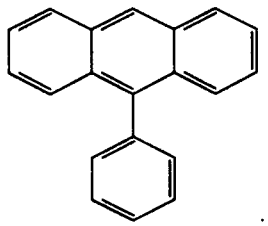

The absorption spectra for the onium salt of Example 1 shows a shift of 0.6 nm from the absorption spectra of the 9-phenylanthracene.

Upon exposure to ultraviolet radiation the onium salts of the invention form Bronsted acids comprising the anion of the salt and a proton from a proton source. The proton source may be intramolecular or intermolecular. The ammonium, phosphonium, sulfonium, selenonium, and arsonium salts of the invention can utilize a separate proton source, such as water, an amine or an alcohol. In a particular embodiment of the invention, sulfonium, selenonium and arsonium salts of the invention include a chromophore which has a releasable, positive hydrogen ion, and can be used without use of an additional material as the proton source. In those onium salts, an intramolecular rearrangement occurs upon exposure to ultraviolet radiation, which results in the formation of a Bronsted acid comprising the anion of the salt and the removable positive hydrogen ion.

The onium salts of the invention can be represented by the following formula:

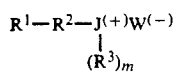

J represents S, Se, SO, SeO, As, N or P. The preferred onium salts of this invention are sulfonium salts. Arsonium and selenonium salts are also highly useful.

$R^1$ is an electron donating chromophore group which absorbs ultraviolet radiation and which exhibits a higher energy occupied molecular orbital than the $R^3$ group or groups. $R^1$ is an aryl or heteroaryl ring system having 3 fused rings. Examples of such rings systems are anthracenyl and phenanthryl moieties. $R^1$ can be substituted. Suitable substituents do not unacceptably degrade the usefulness of the onium salt for the formation of Bronsted acids, for example, by cross-reacting with another substituent or causing steric interference. For example, $R^1$ can be an anthracenyl ring system which includes an F, Cl, I, or Br substituent. $R^1$ can also include, as a substituent, an $R^3$ group. A detailed discussion of $R^3$ groups follows. Specific examples of suitable $R^1$ groups include

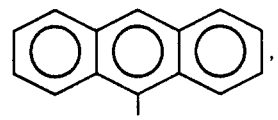

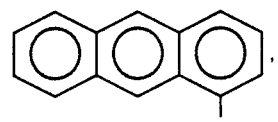

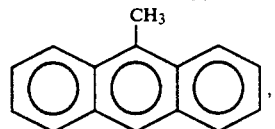

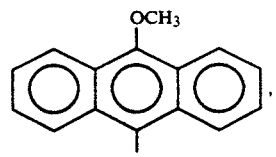

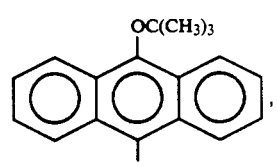

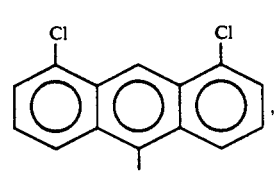

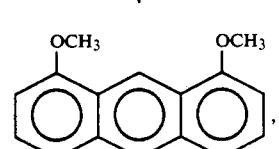

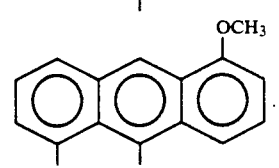

It is desirable that the chromophore be non-basic and the conjugate acid be a "strong acid", that is, the conjugate acid has a pKa of from 0 to −20. Advantageously, $R^1$ includes a hydroxy, chloro nitrile, carbonyl or carboxy group, or an ether or ester group which is weakly basic and in protonated form would be a strong acid.

$R^2$ is the insulating group which substantially prevents π resonance between $R^1$ and the remainder of the compound. $R^2$ is a substituted or unsubstituted arylene or heteroarylene ring system having a solitary ring or two fused rings. Suitable substituents include the same groups as $R^3$. Examples of $R^2$ groups include ortho-, meta-, and para-phenylene.

$R^3$ is an alkyl, aryl, heteroaryl, alkylaryl, or alkylheteroaryl moiety which includes a carbon atom, or more desirably, a —CH$_2$— group directly linked to the S, Se, As, N or P atom. The highest occupied molecular orbital of $R^3$ is not as high as the highest occupied molecular orbital of $R^1$.

$R^3$ has a total of carbons and heteroatoms of from 1 to 25. In the embodiment of the invention disclosed herein, $R^3$ has the general structure —C$_n$H$_{2n}$—(L—R$^4$)$_g$—Z n is an integer from 1 to about 12. g is an integer from 0 to 2. Z is —H, —Cl, —Br, f—F, or —OCH$_3$. $R^4$ is selected from the group consisting of alkylene having from 1 to 12 carbons, and bivalent aryl and heteroaryl ring systems having 1 or 2 solitary, fused or linked rings. Examples of $R^4$ ring systems include phenyl, biphenyl and napthyl. L is a direct link or is selected from the group consisting of —O—, —S—,

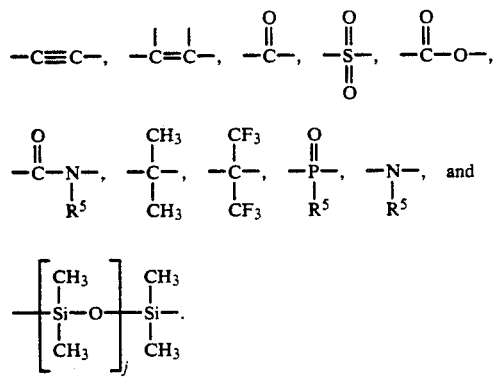

$R^5$ is —H, alkyl having from 1 to 12 carbons, or an aromatic or heteroaromatic ring system having 1 or 2 solitary, fused or linked rings. Examples of $R^3$ groups are alkyls having from 1 to 4 carbon atoms, including the initial —$CH_2$—, substituted with an electron withdrawing group such as halogen; preferably —F, —Cl or —Br; —CN; —$NO_2$; or —$CF_3$; or bridged by a —$SO_2$— linking group.

The number of $R^3$ substituents on J is m, which is an integer equal to 1 minus the valence of $J^{(+)}$. When $J^{(+)}$ is $As^+$, $N^+$, or $P^+$; $J^{(+)}$ calculates as $4-1=3$. When $J^{(+)}$ is $S^+$, $Se^+$, $SO^+$, or $SeO^+$; $J^{(+)}$ calculates as $3-1=2$.

$W^{(-)}$ represents an anion capable of forming a Bronsted acid preferably having a pKa of less than 7. Examples of suitable anions include $BF_4^-$, $ClO_4^-$, $AsF_6^-$, $PF_6^-$, $CH_3SO_3^-$, $CF_3SO_3^-$, $FeCl_4^-$, $BiCl_4^{-2}$, $SnCl_6^{-3}$, $AlF_6^{-3}$, $GaCl_4^-$, $TiF_6^-$, $ZrF_6^-$, $SbF_6^-$, $CH_3CO_2$, $CCl_3CO_2$, $CHCl_2CO_2$, $CH_2ClCO_2$, Cl, Br, F, and paratoluenesulfonate.

The onium salts of the compositions of matter of the invention can be prepared conveniently from aryl aliphatic sulfides and primary aliphatic halides or benzyl halides, by well known methods such as those described in Lowe, P. A., "Synthesis of Sulfonium Salts", The Chemistry of the Sulfonium Group (Part 1), ed. C. J. M. Sterling, John Wiley & Sons, Ltd., (1981), p 267 et seq. In preparing an onium salt by such methods, a solution of the selected sulfide and halide is formed, and a silver salt of the desired anion is then added. For example, silver trifluoromethanesulfonate is used in the synthesis of sulfonium trifluoromethane sulfonate salt. A stochiometric amount of the silver salt is desirably used. The silver salt acts a catalyst for the reaction. While this reaction is occurring the reaction mixture must be protected from exposure to light. Progress of the reaction can be observed by $H^1$-NMR. After the reaction is completed and the silver halide has precipitated it can be removed by filtration or the like.

The reaction mixture may be performed at any temperature however mildly heating the reaction mixture for a moderate length of time, for example, heating to 50° C. for 2 hours can reduce the reaction time. It is convenient to carry out the reaction at atmospheric pressure. Other temperatures and pressures can be used, but should be selected to avoid undesirable results. For example, elevated temperatures may cause an increase in undesirable side reactions.

A variety of solvents can be used, such as acetonitrile, methylene chloride, benzene and ethers such as diethyl ether, however, solvents such as tetrahydrofuran and acetone are undesirable due to sensitivity to the presence of silver cation and Bronsted acids.

Example 1 discloses the preparation of an example of the onium salts of the invention.

The compositions of matter of this invention can be used in any application where it is desirable to release a Bronsted acid. The compositions of matter can include, in addition to the onium salt, a material curable by a Bronsted acid. Such compositions, also called cationically curable compounds, include cyclic formals and acetals, vinyl ethers, cyclic ethers, lactones, polysiloxanes, urea-formaldehyde resins, melamine-formaldehyde resins, and epoxides. A more comprehensive list is detailed in Cationic Polymerization of Olefins: A Critical Inventory J. P. Kennedy, Wiley Interscience Pub. 1975. In the compositions of matter of the invention, the onium salt has a concentration which provides for ultraviolet light absorption throughout the thickness of a layer of the composition. Suitable onium salt percentages by weight of the composition are from 0.1 to 30 or more desirably from 1 to 25. Higher concentrations of onium salt are within the scope of the invention, but may have reduced sensitivity to ultraviolet light due to excessive absorption. The use of thinner films can allow an increase in onium salt concentration.

Epoxy resins are a particularly preferred composition. The useful epoxy resins preferably contain a plurality of epoxy groups and may be based on the reaction product of Bisphenol A, that is, 2,2-bis(4- hydroxyphenyl)propane, and epichlorohydrin, for example, the resins sold under the registered Trademark Araldite by Ciba-Geigy Ltd., or are the reaction product of epichlorohydrin with a phenol-formaldehyde resin of relatively low molecular weight, for example, epoxy-Novolaks (available, for example from Dow), or other modified epoxy resins as disclosed in Uv Curing: Science and Technology (cited above). Still other useful epoxy resins and ether-containing materials polymerizable to a higher molecular weight are listed in Berggren et al, U.S. Pat. No. 4,291,114 (1981) column 4 line 37 through column 6 line 23 and the silicone curable compositions disclosed by Eckberg, U.S. Pat. No. 4,547,431 (1985) column 3 line 29 through column 4 line 17.

In the method of forming images of the invention, a composition of matter of the invention is exposed to ultraviolet radiation on an imagewise basis, that is the exposure is moderated geometrically to provide areas of differing exposure containing image information. The image may be immediately visible, or latent, that is, visible only after further development. The portions of onium salt in the composition, are subject to exposure in the presence of a proton source and are converted to Bronsted acid.

The compositions of matter of the invention can be used to provide protective coatings by imagewise or non-imagewise polymerization of monomers, for example, the epoxide or ether containing monomers referred to above. Overcoats can be provide for optical recording elements, such as those described by Thomas et al, U.S. Pat. No. 4,380,769, issued Apr. 19, 1983. Such recording elements have on a support: (in order), a smoothing layer, a reflection layer, a heat-deformable optical recording layer and a protective overcoat layer.

The method of the invention can be used to make printing plates. For example, a composition of matter of the invention can be provided containing the onium salt and the curable material as a solution which can be solvent coated as a film onto an aluminum substrate. After the film has dried, it can be exposed to light absorbed by the chromophore of the onium salt, thus releasing a Bronsted acid and creating a latent image. The film can be developed to produce a relief image by heating to vaporize chemical fragments from the exposed areas. The raised image can be inked and the resulting plate can be used as a printing plate. The raised image should be capable of being inked and capable of transferring the ink to a substrate, such as paper.

The compositions of matter of the invention are also useful for photoelectrographic elements which have a conductive layer in contact with an acid generating layer which contains the onium salt (the acid generating layer being free of photopolymerizable monomer), as described in Molaire et al, U.S. Pat. No. 4,661,429, issued Apr. 28, 1987. Such elements can be imagewise exposed, the acid photogenerating layer can be electrostatically charged, and the resultant electrostatic image can be developed with charged toning particles. Also, the compositions of matter of the invention are useful for the electrophotographic elements and process described in Scozzofava et al, U.S. Pat. No. 4,485,161, issued Nov. 27, 1984.

The compositions of matter of the invention are useful in making color filter arrays which is described by Molaire et al, U.S. Pat. No. 4,650,734, issued Mar. 17, 1987. In that method, an electrophotographic element having a conductive layer in electrical contact with an acid photogenerating layer comprising an electrically insulating binder and being free of photopolymerizable materials, is imagewise exposed and electrostatically charged to form a latent image, and the latent image is developed with colored toner particles to form a single color array. Those steps can be repeated, with different colored toners to produce a multicolored filter array.

The compositions of matter of the invention are particularly useful to provide photoinitiators to produce imagewise release of chemical fragments in a polymer system for photoresist or printing plate applications.

The following examples are included for a further understanding of the invention.

EXAMPLE 1

Part 1: Preparation of 3-Bromophenyl-butylsulfide

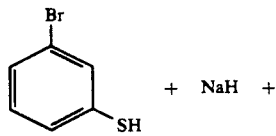

butylbromide →

3-Bromothiophenol (0.2 mole) was dissolved in 100 ml of anhydrous tetrahydrofuran (THF) prior to the addition of 0.2 mole of sodium hydride as a 50% dispersion in mineral oil. The reaction mixture was kept under an argon atmosphere to avoid the formation of disulfides. To the reaction mixture was added 0.2 mole n-butyl bromide in 25 ml of THF. The reaction mixture was stirred for 5 hours at room temperature before flash evaporating off the THF. Diethyl ether (200 ml) and water (100 ml) was added to the reaction mixture. The ether layer was washed with 10% $Na_2CO_3$ to remove the starting thiophenol. The ether layer was dried with magnesium sulfate, filtered and flash evaporated to produce the bromophenyl-butyl sulfide. The sulfide was distilled under reduced pressure to produce 0.18 mole of purified product as a colorless oil.

Part 2: Preparation of 9-(3-Thiobutylphenyl)anthracene

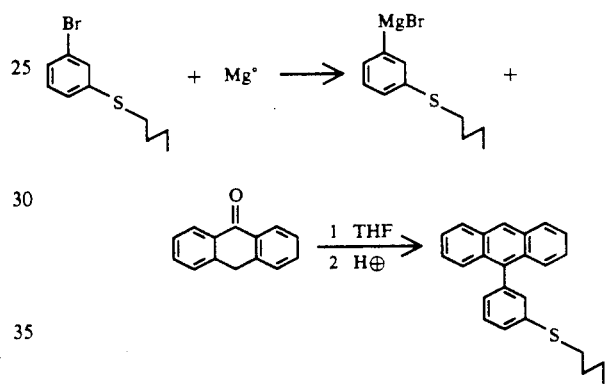

3-Bromophenylbutyl sulfide (0.1 mole) was dissolved in anhydrous THF (100 ml) in a three necked 250 ml flask equipped with a reflux condenser and a dropping funnel. Magnesium metal (0.1 mole) was added to the sulfide and the mixture heated at reflux for 2 hours to form the corresponding Grignard reagent. The reaction mixture was held over an argon atmosphere. To this solution at 0° C. was added anthrone (0.1 mole) as a solid. The reaction mixture was stirred for 15 hours at 0° C. and heated for 1 hour at reflux. HCl (10 ml) was then added to the reaction to produce the elimination of water and formation of the anthracene product. The usual workup produced the phenylanthracene sulfide product in 80% yield.

Part 3: Preparation of 3-(9-Anthryl)phenylmethyl-n-butyl sulfonium trifluoromethane sulfonate

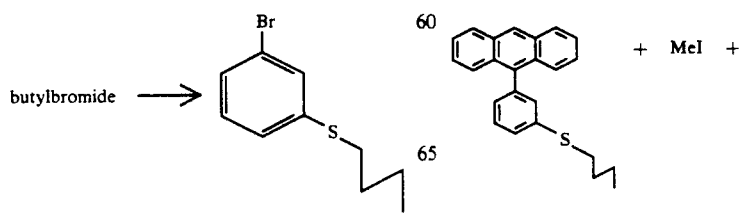

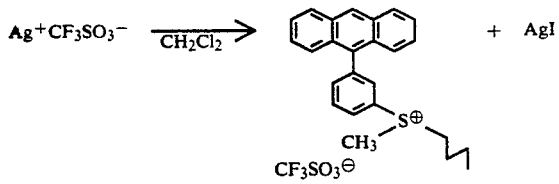

The phenylanthracene sulfide (0.05 mole) was placed in a 100 ml single neck round bottom flask wrapped with aluminum foil to avoid light exposure along with methyl iodide (0.1 mole) and 100 ml $CH_2Cl_2$. To this mixture was added $Ag^+CF_3SO_3^-$ (0.05 ml) as a solid. The reaction mixture was stirred for 15 hours before being filtered to remove AgI. The $CH_2Cl_2$ was removed by flash evaporation. The reaction mixture was dissolved in a minimum amount of $CH_3CN$ (3 ml) and filtered into 300 ml of anhydrous ether. The sulfonium salt product precipitated from solution and was collected by suction filtration (80% yield).

The electronic absorption spectra for the sulfonium salt product and for a free chromophore having a similar structural formula, 9-phenylanthracene, were taken using a Perkin-Elmer lambda 9 spectrophotometer. The 3-(9-anthryl)phenylmethyl-n-butyl sulfonium trifluoromethane sulfonate and 9-phenylanthracene were each dissolved in methylene chloride to provide a $10^{-4}$ Molar solutions and placed in a 1 centimeter rectangular optical cell. The spectra are shown in the Figure, in which optical density in absorption units is plotted against wavelength in nanometers.

The following examples show the use of the salts of the invention to produce images, by the imagewise release of chemical fragments in a polymer system for photoresist applications.

EXAMPLE 2

Imagewise Release of a Chemical Fragment 3-(9-Anthryl)phenylmethyl-n-butyl sulfonium trifluoromethane sulfonate (10% by weight) was dissolved in sufficient acetonitrile solvent along with polyvinyl (4-t-butylphenyl-carbonate) as host polymer (90% by weight) to make a homogeneous solution. A film of the polymer-photoacid composition was cast onto a silicon wafer. The film was then irradiated in an imagewise fashion with a Hg light source. In the irradiated areas a Bronsted acid was produced which catalyzed the thermal transformation of the original polymer to polyvinylphenol after heating at 100° C. for 5–15 minutes. The regions containing the polyvinylphenol were then selectively removed with an aqueous base solution (10–50% hydroxide solution).

EXAMPLE 3

Predictive Example of Imagewise Release of a Silane Chemical Fragment 2-(9-Anthryl)phenyldimethyl sulfonium trifluoromethane sulfonate (10% by weight) would be dissolved in sufficient dichloromethane along with a polymer containing pendant allyl-t-butyldimethyl silyl groups (90% by weight) to make a homogeneous solution. A film of the polymer-photoacid composition would be cast onto a silicon wafer. The film would then be irradiated in an imagewise fashion using a He-Xe lamp. In the irradiated area a Bronsted acid would be produced which would catalyze the thermal transformation to the vinyl polymer without the pendant silane functionality. Exposure of the irradiated and heated film to an oxygen plasma would selectively remove the irradiated areas by a completely dry process.

EXAMPLE 4

Imagewise Release of a Chemical Fragment 3-(9-Anthryl)phenyldimethyl sulfonium trifluoromethane sulfonate (10% by weight) was dissolved in sufficient acetonitrile solvent along with polyvinyl (4-t-butylphenylcarbonate) as host polymer (90% by weight) to make a homogeneous solution. A film of the polymer-photoacid composition was cast onto a silicon wafer. The film was then irradiated in an imagewise fashion with a 200 Watt Hg-Xe light source. In the irradiated areas a Bronsted acid was produced which catalyzed the thermal transformation of the original polymer to polyvinylphenol after heating at 100° C. for 5–15 minutes. The regions containing the polyvinylphenol were then selectively removed with an aqueous base solution (10–50% hydroxide solution).

EXAMPLE 5

Predictive Example of Imagewise Release of a Silane Chemical Fragment 4-(9-Anthryl)phenyldimethyl sulfonium trifluoromethane sulfonate (10% by weight) would be mixed with a polymer containing pendant allyl-t-butyldimethyl silyl groups (90 % by weight) to make a homogeneous solution. A film of the polymer photoacid composition would be cast onto a silicon wafer. The film would then be irradiated in an imagewise fashion using a 200 Watt Hg-Xe lamp. In the irradiated area a Bronsted acid would be produced which would catalyze the thermal transformation to the vinyl polymer without the pendant silane functionality. Exposure of the irradiated and heated film to an oxygen plasma would selectively remove the irradiated areas by a completely dry process.

Results similar to those described in the above examples can be obtained with other sulfonium and arsonium salts of the type described above. Also, by employing a protonating material such as water or an alcohol, similar results can be obtained with the phosphonium and ammonium salts described above, and with the sulfonium, selenonium and arsonium salts described above but in which the chromophore does not contain a removable, positive hydrogen ion.

The following examples illustrate compositions of matter which can provide polymer coatings by photoinduced cationic polymerization of epoxide monomers and prepolymers.

EXAMPLE 6

2-(9-Anthryl)phenylmethyl-n-butyl sulfonium trifluoromethane sulfonate (0.1 grams) was dissolved in methylene chloride (10 ml) along with cyclohexene oxide (1.0 grams) and the mixture was coated onto a glass substrate and irradiated with visible light from a 200 Watt Hg-Xe lamp positioned 4" from the substrate. The solution polymerized after exposure to ultraviolet radiation for 1 minute and heating at 50° C. for 30 minutes. Polymerization was initiated by the Bronsted acid released when the sulfonium salt was irradiated.

EXAMPLE 7

3-(9-Anthryl)phenylmethyl-isobutyl sulfonium hexafluorophosphate (0.2 grams) was dissolved in methylene chloride (2 ml) along with an epoxy prepolymer (1.0 grams). A film of the prepolymer sulfonium sensitizer composition was formed on a glass substrate by spin coating. The thin film (0.5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

EXAMPLE 8

3-(9-Anthryl)phenyldimethyl sulfonium hexafluorophosphate (0.2 grams) was dissolved in methylene chloride (2 ml) along with an epoxy prepolymer (1.0 grams). A film of the prepolymer-sulfonium sensitizer composition was formed on a glass substrate by spin coating. The thin film (0.5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

EXAMPLE 9

2-(9-Anthryl)phenyldimethyl sulfonium trifluoromethane sulfonate (0.2 grams) was dissolved in methylene chloride (2 ml) along with an epoxy prepolymer (1.0 grams). A film of the prepolymer-sulfonium sensitizer composition was formed on a glass substrate by spin coating. The thin film (0.5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

EXAMPLE 10 (PREDICTIVE EXAMPLE)

3-(9-Anthryl)phenyldimethyl arsonium hexafluorophosphate (0.2 grams) would be dissolved in methylene chloride (2 ml) along with an epoxy prepolymer (1.0 grams). A film of the prepolymer-sulfonium sensitizer composition would be formed on a glass substrate by spin coating. The thin film (0.5 micrometers) would be irradiated for 2 minutes with a 200 Watt Hg-Xe lamp as previously described. The polymer film would become tough and cross-linked after heating at 50° C. for 30 minutes. Cross-linking would be initiated by the Bronsted acid released when the sulfonium salt was irradiated.

The following examples illustrate the formation of images by imagewise dye absorption changes as a result of dye protonation.

EXAMPLE 11

4-(9-Anthryl)phenylmethyl propyl sulfonium trifluoromethane sulfonate (1.0 grams) was dissolved in methylene chloride (5 ml) along with polystyrene, MW=100,000, (1.0 grams) and propyl red indicator (0.001 grams). A film of the above composition was formed on a 1" round disc (⅛ inch thick) by spin coating. The polymer film was then exposed to visible light from a Hg-Xe lamp positioned 4" from the substrate for 3 minutes. The initially yellow film turned red after the irradiation was complete as a result of the Bronsted acid released from the sulfonium salt and protonation of the propyl red indicator.

EXAMPLE 12

3-(9-Anthryl)phenyldimethyl sulfonium trifluoromethane sulfonate (1.0 grams) was dissolved in methylene chloride (5 ml) along with polystyrene, MW=100,000, (1.0 grams) and propyl red indicator (0.001 grams). A film of the above composition was formed on a 1" round disc (⅛ inch thick) by spin coating. The polymer film was then exposed to visible light from a Hg-Xe lamp positioned 4" from the substrate for 3 minutes. The initially yellow film turned red after the irradiation was complete as a result of the Bronsted acid released from the sulfonium salt and protonation of the propyl red indicator.

The following examples illustrate the formation of images, specifically, imagewise conductive films for electrophotographic copying, circuit board fabrication, and fabrication of color filter arrays.

EXAMPLE 13

3-(9-Anthryl)phenylmethyl-n-propyl sulfonium hexafluorophosphate (0.1 grams) was dissolved in methylene chloride (5 ml) along with polystyrene, MW=100,000, (1.0 grams). A film of the above composition was cast onto a conductive substrate of either aluminum or nesa (InSnO) glass by spin coating. The solvent was allowed to evaporate in a vacuum oven with heating (25°-50° C. for 30 minutes). The polymer film was then exposed to visible light from a Hg-Xe lamp through a mask for 1 minute. The film was then charged with either a positive or negative corona while the conductive layer was held to ground. The ion-charge discharges more rapidly in the irradiated areas due to the presence of a Bronsted acid to produce a latent charged image which can be visualized by the conventional toning procedure. Transfer of the toned image to paper converts it to a permanent state. Additional copies of the charged image can be made by repeating the charging, toning, and transfer process without repeating the exposure step.

EXAMPLE 14

4-(9-Anthryl)phenylmethyl-n-butyl sulfonium hexafluorophosphate (0.1 grams) was dissolved in methylene chloride (5 ml) along with polystyrene, MW=100,000, (1.0 grams). A film of the above composition was cast onto a conductive substrate of either aluminum or nesa (InSnO) glass by spin coating. The solvent was allowed to evaporate in a vacuum oven with heating (25°-50° C. for 30 minutes). The polymer film was then exposed to light from a Hg-Xe lamp through a mask for 1 minute. The film was then charged with either a positive or negative corona while the conductive layer was held to ground. The ion-charge discharges more rapidly in the irradiated areas due to the presence of a Bronsted acid to produce a latent image which can be visualized by the conventional toning procedure. Transfer of the toned image to paper converts it to a permanent state. Additional copies of the charged image can be made by repeating the charging, toning, and transfer process without repeating the exposure step.

The following examples illustrate the use of Bronsted photoacids for the production of images in the form of printing plate masters.

EXAMPLE 15

Predictive Example of Printing Plate Masters 3-(9-Anthryl)phenyldimethyl sulfonium trifluoromethane sulfonate (10% by weight) would be dissolved in sufficient acetonitrile solvent along with polyvinyl-(4-t-butylphenylcarbonate) as host polymer (90% by weight) to make a homogeneous solution. A film (0.5 microns) of the polymer-photoacid composite would be cast onto a flexible rectangular aluminum substrate 10"×12" in dimensions. After drying at 50° C. for 10 minutes, the film would be exposed in an imagewise fashion with a 200 Watt Hg-Xe lamp. Development to produce a relief image in the exposed areas would be achieved by heating the film to 100° C. for 5 minutes. The aluminum substrate would be then wrapped around a drum with the relief image exposed. The raised pattern could be selectively inked and the inked image transferred to a substrate such as paper. This process could be repeated many times.

EXAMPLE 16

Predictive Example of Printing Plate Masters 3-(9-Anthryl)phenyldimethyl sulfonium trifluoromethane sulfonate (10% by weight) would be dissolved in sufficient acetonitrile solvent along with polyvinyl-(4-t-butylphenylcarbonate) as host polymer (90% by weight) to make a homogeneous solution. A film (0.5 microns) of the polymer-photoacid composite would be cast onto a flexible rectangular aluminum substrate 10"×12" in dimensions. After drying at 50° C. for 10 minutes, the film would be exposed in an imagewise fashion with a 200 Watt Hg-Xe lamp. Development to produce a relief image in the exposed areas would be achieved by heating the film to 100° C. for 5 minutes. The aluminum substrate would be then wrapped around a drum with the relief image exposed. The raised pattern could be selectively inked and the inked image transferred to a substrate such as paper. This process could be repeated many times.

EXAMPLE 17

Printed Circuit Board Fabrication 4-(9-Anthryl)phenylmethyl-n-butyl sulfonium trifluoromethane sulfonate (0.1 grams) and poly(4-t-butylphenylcarbonate) (1.9 grams) were dissolved in 5 ml of dichloromethane. A 1 mil film of the above composition was cast onto a copper substrate and allowed to dry for 15 minutes at 60° C. The film was exposed for two minutes in an imagewise fashion through a test target with a 200 Watt Hg-Xe lamp. The film was heat treated at 100° C. for 1 minute before development to remove the exposed regions with a 20% $Na_2CO_3$ solution. The exposed copper was etched with a nitric acid solution in the presence of molecular oxygen to produce a copper pattern for a printed circuit board.

This invention has been described in detail with particular reference to preferred embodiments thereof, but it will be understood that variations and modifications can be affected within the spirit and scope of the invention.

What is claimed is:

1. An onium salt having the general formula:

wherein:
$W^{(-)}$ is an anion;
$R^1$ is a substituted or unsubstituted aryl or heteroaryl ring system having three fused rings;
$R^2$ is a substituted or unsubstituted arylene or heteroarylene ring system having a single ring or two fused rings;
n in each $C_nH_{2n}$ group is an integer from 1 to about 12 independent of the value of n in the other $C_nH_{2n}$ group;
each g is independently an integer from 0 to 2;
each Z is independently H, Cl, Br, F, or $OCH_3$;
each $R^4$ is independently alkylene having from 1 to carbons; and
each L is independently a direct link or is selected from the group consisting of

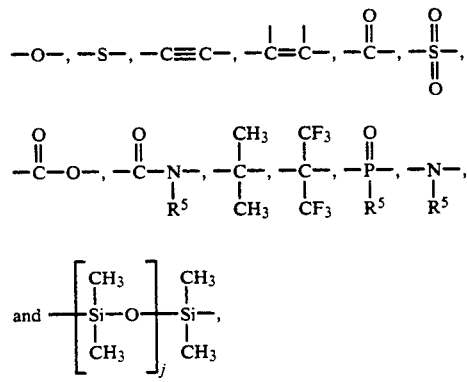

wherein n is an integer from 1 to 11, each $R^5$ is independently selected from the group consisting of —H, alkyl having from 1 to 12 carbons, and aromatic and heteroaromatic ring systems having 1 or 2 solitary, fused or linked rings, m is an integer from 1 to 12, and j is an integer from 0 to 10; with the provisos
that $R^1$ is an electron donating group which can absorb ultraviolet radiation and exhibit a higher energy occupied molecular orbital than said

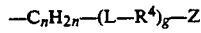

groups:
that if n=1, g=0; and
that the onium salt is capable of forming a Bronsted acid upon exposure to ultraviolet radiation in the presence of a proton source.

2. The onium salt of claim 1 further characterized in that said onium salt exhibits a shift in absorbance of less than 15 nanometers from the electronic absorption spectrum of a compound having the same structure as $R^1$, with the exception that the bond to $R^2$ is replaced by H.

3. The onium salt of claim 1 further characterized in that said onium salt exhibits a shift in absorbance of less than 10 nanometers from the electronic absorption spectrum of a compound having the same structure as $R^1$, with the exception that the bond to $R^2$ is replaced by H; and the onium salt is capable of forming a Bronsted acid upon exposure to ultraviolet radiation in the presence of a proton source.

4. The onium salt of claim 1 wherein g=0.

5. The onium salt of claim 4 wherein Z=H.

6. The onium salt of claim 1 wherein $R^2$ is phenylene or naphthalene.

7. The onium salt of claim 6 wherein $R^1$ has a substituent selected from the group consisting of hydroxy, chloro, nitrile, carbonyl and carboxy.

8. The onium salt of claim 7 wherein g is 0 and Z is —H.

9. The onium salt of claim 1 wherein:
$R^1$ is selected from the group consisting of

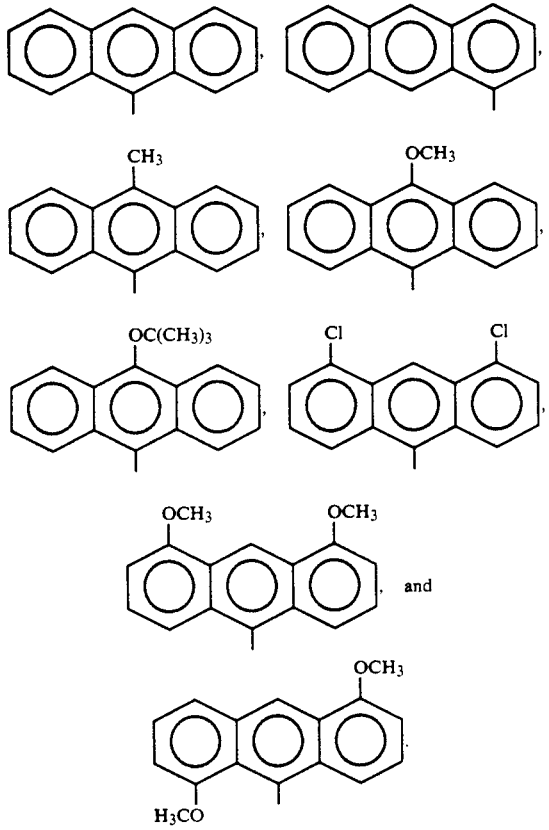

10. The onium salt of claim 9 wherein $R^2$ is ortho-phenylene, meta-phenylene or para-phenylene.

11. The onium salt of claim 10 wherein $W^{(-)}$ represents $BF_4^-$, $ClO_4^-$, $AsF_6^-$, $PF_6^-$, $CH_3SO_3^-$, $CF_3SO_3^-$, $FeCl_4^-$, $BiCl_4^{-2}$, $SnCl_6^{-3}$, $AlF_6^{-3}$, $GaCl_4^-$, $TiF_6^-$, $ZrF_6^-$, $SbF_6^-$, $CH_3CO_2$, $CCl_3CO_2$, $CHCl_2CO_2$, $CH_2ClCO_2$, Cl, Br, F, and paratoluenesulfonate.

12. The onium salt of claim 1 wherein said onium salt is 3-{9-anthryl}phenylmethyl-n-butyl sulfonium trifluoromethane sulfonate.

13. The onium salt of claim 1 wherein said onium salt is 4-hexafluorophosphate.

14. An onium salt having the general formula:

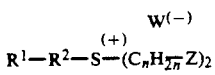

wherein:
$W^{(-)}$ is an anion;

$R^1$ is a chromophore which absorbs ultraviolet light;

$R^2$ is a substituted or unsubstituted arylene or heteroarylene ring system having a single ring or two fused rings;

n in each —$C_nH_{2n}$—Z group is an integer from 1 to about 12 independent of the value of n in the other —$C_nH_{2n}$—Z group; and each Z is independently H, Cl, Br, F, or $OCH_3$; with the provisos that $R^1$ is an electron donating group which can absorb ultraviolet radiation and exhibit a higher energy occupied molecular orbital than said —$C_nH_{2n}$—Z groups; and that the onium salt is capable of forming a Bronsted acid upon exposure to ultraviolet radiation in the presence of a proton source.

15. The onium salt of claim 14 wherein $R^1$ has a removable positive hydrogen ion, whereby said salt is capable, upon exposure to ultraviolet radiation, of forming by an intramolecular rearrangement, a Bronsted acid comprising the anion of said salt and said removable hydrogen ion.

16. The onium salt of claim 14 wherein $R^1$ is a substituted or unsubstituted aryl or heteroaryl ring system having three fused rings and each n is independently an integer from 1 to 4.

17. The onium salt of claim 14 wherein the electronic absorption spectrum of the onium salt exhibits a shift in absorbance of less than 15 nanometers from the electronic absorption spectrum of a chromophore having the same structure as $R^1$, with the exception that the bond to $R^2$ is replaced by H.

18. An onium salt, capable of forming a Bronsted acid upon exposure to ultraviolet radiation in the presence of a proton source, said onium salt having the general formula:

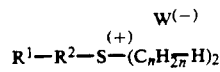

wherein:
$W^{(-)}$ is an anion;

$R^1$ is a substituted anthracenyl or phenanthryl ring system;

$R^2$ is phenylene;

n in each —$C_nH_{2n}$—H group is an integer from 1 to about 12 independent of the value of n in the other —$C_nH_{2n}$—H group.

* * * * *

UNITED STATES PATENT AND TRADEMARK OFFICE
CERTIFICATE OF CORRECTION

PATENT NO. : 5,302,757
DATED : April 12, 1994
INVENTOR(S) : Franklin Donald Saeva It is certified that error appears in the above-identified patent and that said Letters Patent is hereby corrected as shown below:

Column 16, line 2 reads " is 4-hexafluorophosphate" should read --is 4-(9-anthryl) phenylmethyl-n-butyl sulfonium hexafluorophosphate--.

Signed and Sealed this

Eleventh Day of October, 1994

Attest:

BRUCE LEHMAN

Attesting Officer

Commissioner of Patents and Trademarks